United States Patent
Harada et al.

(10) Patent No.: US 9,486,411 B2
(45) Date of Patent: Nov. 8, 2016

(54) SOLID PREPARATION

(71) Applicant: Takeda Pharmaceutical Company Limited, Chuo-ku, Osaka-shi, Osaka (JP)

(72) Inventors: Maiko Harada, Osaka (JP); Ikurou Yamane, Osaka (JP); Masafumi Misaki, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/405,500

(22) PCT Filed: Jun. 4, 2013

(86) PCT No.: PCT/JP2013/065905
§ 371 (c)(1),
(2) Date: Dec. 4, 2014

(87) PCT Pub. No.: WO2013/183784
PCT Pub. Date: Dec. 12, 2013

(65) Prior Publication Data
US 2015/0141447 A1    May 21, 2015

(30) Foreign Application Priority Data

Jun. 5, 2012  (JP) ................. 2012-128360

(51) Int. Cl.
*A61K 31/513*  (2006.01)
*A61K 9/16*    (2006.01)
*A61K 9/20*    (2006.01)
*A61K 9/28*    (2006.01)

(52) U.S. Cl.
CPC ........... *A61K 9/2054* (2013.01); *A61K 9/1652* (2013.01); *A61K 9/2013* (2013.01); *A61K 9/2018* (2013.01); *A61K 9/2077* (2013.01); *A61K 9/284* (2013.01); *A61K 9/2866* (2013.01); *A61K 31/513* (2013.01)

(58) Field of Classification Search
CPC ............. A61K 31/513; A61K 9/1652; A61K 9/2013; A61K 9/2018; A61K 9/2054; A61K 9/2077; A61K 9/284; A61K 9/2866
See application file for complete search history.

(56) References Cited

U.S. PATENT DOCUMENTS

| | | |
|---|---|---|
| 2005/0261271 A1 | 11/2005 | Feng et al. |
| 2007/0060530 A1 | 3/2007 | Christopher et al. |
| 2008/0227798 A1 | 9/2008 | Kelly et al. |
| 2008/0280931 A1 | 11/2008 | Kelly et al. |
| 2008/0287476 A1 | 11/2008 | Christopher et al. |
| 2012/0129878 A1 | 5/2012 | Murakawa et al. |

FOREIGN PATENT DOCUMENTS

| | | | |
|---|---|---|---|
| WO | WO 02/03987 A2 | 1/2002 | |
| WO | WO 2005/067976 A2 | 7/2005 | |
| WO | WO 2006/078593 A2 | 7/2006 | |
| WO | WO 2007/128724 A1 | 11/2007 | |
| WO | WO 2008/114800 * | 9/2008 | ............ A61K 9/20 |
| WO | WO 2008/114800 A8 | 9/2008 | |
| WO | WO 2011/013639 A1 | 2/2011 | |
| WO | WO 2012/062691 A1 | 5/2012 | |

OTHER PUBLICATIONS

Chowhan, et al., Drug-excipient interactions resulting from powder mixing. IV: Role of lubricants and their effect on in vitro dissolution, J. of Pharm. Sci. vol. 75, No. 6, 542-545, XP002702950 (1986).*
Kuno, et al., Effect of the type of lubricant on the characteristics of orally disintegrating tablets manufactured using the phase transition of sugar alcohol, European J. of Pharm. and Biopharm., vol. 69, No. 3, 986-992, XP023519560 (2008).*
Michoel, et al., Comparative evaluation of co-processed lactose and microcrystalline cellulose with their physical mixtures in the formulation of folic acid tablets, Pharm. Dev. and Tech., vol. 7, No. 1, XP009124078 (2002).*
Chowhan et al., "Drug-Excipient Interactions Resulting from Powder Mixing IV: Role of Lubricants and Their Effect on In Vitro Dissolution," Journal of Pharmaceutical Sciences, Jun. 1986, 75(6):542-545.
Kuno et al., "Effect of the type of lubricant on the characteristics of orally disintegrating tablets manufactured using the phase transition of sugar alcohol," European Journal of Pharmaceutics and Biopharmaceutics, Aug. 1, 2008, 69(3):986-992.
Michoel et al., "Comparative Evaluation of Co-processed Lactose and Microcrystalline Cellulose with Their Physical Mixtures in the Formulation of Folic Acid Tablets," Pharmaceutical Development and Technology, Jan. 1, 2002, 7(1):79-87.

* cited by examiner

*Primary Examiner* — Erich A Leeser
(74) *Attorney, Agent, or Firm* — Foley & Lardner LLP

(57) ABSTRACT

The present invention provides a solid preparation excellent in disintegration property and preservation stability. The present invention relates to a solid preparation containing (1) 2-[[6-[(3R)-3-amino-1-piperidinyl]-3,4-dihydro-3-methyl-2,4-dioxo-1(2H)-pyrimidinyl]methyl]-4-fluorobenzonitrile (compound (A)) or a salt thereof, (2) a saccharide, and (3) sodium stearyl fumarate. In addition, the present invention relates to a solid preparation containing (1) compound (A) or a salt thereof, (2) a saccharide, and (3) stearic acid or talc in a naked tablet part.

9 Claims, No Drawings

SOLID PREPARATION

TECHNICAL FIELD

The present invention relates to a solid preparation comprising 2-[[6-[(3R)-3-amino-1-piperidinyl]-3,4-dihydro-3-methyl-2,4-dioxo-1(2H)-pyrimidinyl]methyl]-4-fluorobenzonitrile (sometimes to be abbreviated as "compound (A)" in the present specification) or a salt thereof and the like.

BACKGROUND OF THE INVENTION

Compound (A) is a compound represented by the following formula:

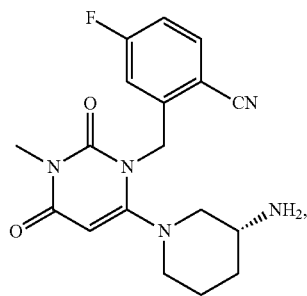 [SMILES: Cn1c(=O)cc(N2CCC[C@@H](N)C2)n(Cc2cc(F)ccc2C#N)c1=O]

Compound (A) or a salt thereof has been reported as an inhibitor of dipeptidyl peptidase (DPP-IV), which is an enzyme that decomposes glucagon-like peptide-1 (GLP-1), a hormone increasing insulin secretion (patent document 1). In addition, a method including administering 1-250 mg of compound (A) or a salt thereof to a patient once per week (patent documents 2, 3), crystal polymorphs of compound (A) (patent documents 4, 5), and a preparation of compound (A) (patent documents 6, 7) have also been reported. Compound (A) and a salt thereof are recommended for oral administration in view of the easiness of self-administration, and a tablet, particularly a tablet in the dosage form for administration once per week, is desired.

The dosage form of once per week is expected to improve drug compliance of patients, whereas it requires supply of compound (A) or a salt thereof to patients in a high dose as compared to, for example, the dosage form of once per day. Since a solid preparation containing compound (A) or a salt thereof in a high dose increases its size, it may conversely degrade the drug compliance for patients, particularly infants and elderly patients having difficulty in swallowing.

DOCUMENT LIST

Patent Documents patent document 1: US2005/0261271
patent document 2: US2007/0060530
patent document 3: US2008/0287476
patent document 4: US2008/0227798
patent document 5: US2008/0280931
patent document 6: WO2008/114800
patent document 7: WO2011/013639

SUMMARY OF THE INVENTION

Therefore, the development of a compact solid preparation having a high content of compound (A) or a salt thereof as a pharmaceutical product with high drug compliance of patients is desired.

The present inventors have conducted various studies of a compact solid preparation having a high content of compound (A) or a salt thereof and found that the preparation is associated with poor disintegrability and a decrease in the preservation stability (delay of dissolution and delay of disintegration after preservation under high humidity). Such poor disintegrability and a decrease in the preservation stability degrade the disintegration property and dissolution property of the solid preparation in the stomach, decrease the amount of the active ingredient absorbed in the body, and decrease the efficacy. It is therefore an object of the present invention to provide a compact solid preparation having a high content of compound (A) or a salt thereof, which does not show poor disintegrability and a decrease in the preservation stability.

The present inventors have conducted intensive studies in an attempt to solve the aforementioned problems and succeeded in miniaturizing a solid preparation with a high content of compound (A) or a salt thereof by using a saccharide and sodium stearyl fumarate, and further found that a solid preparation excellent in the disintegration property and preservation stability can be provided, which resulted in the completion of the present invention.

Accordingly, the present invention is as follows.
[1] A solid preparation comprising
(1)  2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof,
(2) a saccharide and
(3) sodium stearyl fumarate
(hereinafter sometimes to be abbreviated as the solid preparation of the present invention).
[2] The solid preparation of the above-mentioned [1], wherein the saccharide is mannitol.
[3] The solid preparation of the above-mentioned [1] or [2], wherein the content of 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof is 50-60 wt %.
[4] The solid preparation of the above-mentioned [1], [2] or [3], further comprising crystalline cellulose, croscarmellose sodium and hydroxypropylcellulose.
[5] A solid preparation comprising
(1)  2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof,
(2) a saccharide and
(3) stearic acid or talc
in a naked tablet part
(hereinafter sometimes to be abbreviated as the solid preparation P of the present invention).
[6] The solid preparation of the above-mentioned [5], wherein the saccharide is mannitol.
[7] The solid preparation of the above-mentioned [5] or [6], wherein the content of 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof is 50-60 wt %.

Effect of the Invention

According to the present invention, a solid preparation comprising compound (A) or a salt thereof as an active ingredient in a high content (50-60 wt %), which is excellent in the disintegration property and preservation stability can be provided. The solid preparation of the present invention and the solid preparation P of the present invention are excellent in the dissolution property of the active ingredient even when preserved at a high temperature (for example, 60° C.) under high humidity (for example, 75% RH) for a long term (for example, 2 weeks).

In addition, the solid preparation of the present invention and the solid preparation P of the present invention are excellent in the disintegration property even when they are preserved at a high temperature (for example, 60° C.) under high humidity (for example, 75% RH) for a long term (for example, 2 weeks).

DETAILED DESCRIPTION OF THE INVENTION

The present invention is explained in detail in the following.

Compound (A) or a salt thereof can be produced by a known method, for example, the method described in WO2007/035629 or a method analogous thereto.

Examples of the salt of compound (A) include a pharmacologically acceptable salt, such as a salt with inorganic acid, a salt with organic acid, a salt with basic or acidic amino acid and the like.

Preferable examples of the salt with an inorganic acid include salts with hydrochloric acid, hydrobromic acid, nitric acid, sulfuric acid, phosphoric acid and the like.

Preferable examples of the salt with an organic acid include salts with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with a basic amino acid include salts with arginine, lysine, ornithine and the like. Preferable examples of the salt with an acidic amino acid include salts with aspartic acid, glutamic acid and the like.

Preferable examples of the salt of compound (A) include salts with trifluoroacetic acid, succinic acid, hydrochloric acid and the like. Of these, succinate of compound (A) is preferable, and monosuccinate of compound (A) is more preferable.

As compound (A) or a salt thereof, succinate of compound (A) is preferable.

Compound (A) may be a solvate (e.g., hydrate) or non-solvate (e.g., non-hydrate).

Compound (A) may be labeled with an isotope (e.g., $^3H$, $^{35}S$, $^{125}I$).

Furthermore, a deuterium-converted compound wherein $^1H$ has been converted to $^2H(D)$ is also encompassed in the compound (A).

The content of compound (A) or a salt thereof in the solid preparation of the present invention and the solid preparation P of the present invention is 50-60 wt %, more preferably 52-56 wt %, as compound (A) (free form).

The solid preparation of the present invention and the solid preparation P of the present invention contain a saccharide. Examples of the saccharide to be used in the present invention include sugar alcohol and sugar.

Examples of the sugar alcohol include mannitol, maltitol, sorbitol, erythritol, xylitol and the like, with preference given to mannitol.

Examples of the sugar include lactose, sucrose, glucose, maltose, sucrose, trehalose and the like, with preference given to lactose.

As the saccharide in the solid preparation of the present invention and the solid preparation P of the present invention, sugar alcohol is preferable, and mannitol is particularly preferable.

The content of the saccharide in the solid preparation of the present invention and the solid preparation P of the present invention is generally 1-30 wt %, preferably 2-20 wt %, more preferably 3-10 wt %.

The solid preparation of the present invention contains sodium stearyl fumarate.

The content of sodium stearyl fumarate in the solid preparation of the present invention is generally 0.3-7 wt %, preferably 0.5-5 wt %, more preferably 1.0-3.0 wt %.

The solid preparation of the present invention is preferably a solid preparation comprising
(1) 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof,
(2) a saccharide and
(3) sodium stearyl fumarate
in a naked tablet part.

The solid preparation of the present invention is more preferably a solid preparation comprising
(1) 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof,
(2) mannitol and
(3) sodium stearyl fumarate
in a naked tablet part.

In the present specification, the naked tablet (plain tablet) means a tablet obtained by adding additive(s) such as excipient, binder, disintegrant, lubricant and the like to compound (A) or a salt thereof, mixing them and compressing the mixture.

In the present invention, the naked tablet is different from a film-coated tablet in that it is not subjected to film coating. Here, film coating means coating the surface of naked tablet with coating layer not containing an active ingredient.

The solid preparation of the present invention and the solid preparation P of the present invention may contain a pharmaceutically acceptable carrier in addition to the above-mentioned components, as long as it does not inhibit the effect of the present invention. As the pharmaceutically acceptable carrier, various organic or inorganic carrier substances conventionally used as preparation materials can be used. They are appropriately added as, for example, excipient, binder, disintegrant, glidant, lubricant, colorant, pH adjusting agent, surfactant, stabilizer, acidulant, flavor, coating base or coating additive in an appropriate amount.

Examples of the excipient include crystalline cellulose, starches such as cornstarch, potato starch, wheat starch, rice starch, partly pregelatinized starch, pregelatinized starch, porous starch and the like; light anhydrous silicic acid, dextrin, carboxymethylstarch, gelatin, magnesium oxide, calcium hydrogen phosphate, anhydrous calcium hydrogen phosphate, calcium carbonate and calcium sulfate, and crystalline cellulose is more preferable.

The content of the excipient in the solid preparation of the present invention and the solid preparation P of the present invention is preferably 1-30 wt %, more preferably 2-15 wt %.

The binder only needs to be an additive capable of binding particles during dry or wet granulation and direct tableting and, for example, hydroxypropylcellulose [e.g., grade: L, SL, SSL (trade name); Nippon Soda Co., Ltd.], hydroxypropylmethylcellulose [e.g., hypromellose 2910, TC-5 (grade: MW, E, EW, R, RW) (trade name); Shin-Etsu Chemical Co., Ltd.], povidone (polyvinylpyrrolidone), copolyvidone and the like can be mentioned. Hydroxypropylcellulose, hydroxypropylmethylcellulose or povidone is preferable, and hydroxypropylcellulose is more preferable.

The content of the binder in the solid preparation of the present invention and the solid preparation P of the present invention is preferably 0.5-15 wt %, more preferably 1-10 wt %.

Examples of the disintegrant include carboxymethylcellulose, calcium carboxymethylcellulose, sodium carboxymethyl starch, croscarmellose sodium [e.g., Ac-Di-Sol (trade name); Dainippon Sumitomo Pharma Co., Ltd.], crospovidone, low-substituted hydroxypropylcellulose, hydroxypropylstarch and the like, more preferably croscarmellose sodium.

The content of the disintegrant in the solid preparation of the present invention and the solid preparation P of the present invention is preferably 1-30 wt %, more preferably 2-20 wt %.

Examples of the glidant include talc, light anhydrous silicic acid, hydrated silicon dioxide and magnesium aluminometasilicate.

Examples of the lubricant include stearic acid, magnesium stearate, calcium stearate, sucrose ester of fatty acid, talc, waxes, DL-leucine, sodium lauryl sulfate, magnesium lauryl sulfate, macrogol 6000 and light anhydrous silicic acid.

Preferable examples of the colorant include food colors such as Food Color Yellow No. 5, Food Color Red No. 2, Food Color Blue. No. 2 and the like; food lake colors, red ferric oxide, yellow ferric oxide and the like.

Preferable examples of the pH adjusting agent include citric acid and a salt thereof, phosphoric acid and a salt thereof, carbonic acid and a salt thereof, tartaric acid and a salt thereof, fumaric acid and a salt thereof, acetic acid and a salt thereof, amino acid and a salt thereof and the like.

Preferable examples of the surfactant include sodium lauryl sulfate, polysorbate 80, polyoxyethylene(160)polyoxypropylene(30)glycol and the like.

Preferable examples of the stabilizer include succinic acid, tartaric acid, citric acid, lactic acid, fumaric acid, malic acid, ascorbic acid, acetic acid, acidic amino acid (e.g., glutamic acid, aspartic acid), inorganic salts of these acids (e.g., alkali metal salt, alkaline earth metal salt), salts with inorganic bases (e.g., ammonium) of these acids, salts with organic bases (e.g., meglumine) of these acids, salts with basic amino acid (e.g., arginine, lysine, ornithine) of these acids, hydrates thereof, solvates thereof and the like.

Preferable examples of the acidulant include ascorbic acid, citric acid, tartaric acid, malic acid and the like.

Preferable examples of the flavor include menthol, peppermint oil, lemon oil, vanillin and the like.

Preferable examples of the coating base include a sugar coating base, a water-soluble film coating base, an enteric film coating base, a sustained-release film coating base and the like.

As the sugar coating base, for example, purified sucrose is used. Furthermore, one or more kinds selected from talc, precipitated calcium carbonate, gelatin, gum arabic, pullulan, carnauba wax and the like may be used in combination.

Examples of the water-soluble film coating base include cellulose polymers such as hydroxypropylcellulose [e.g., grade: L, SL, SL-T, SSL (trade name); Nippon Soda Co., Ltd.], hydroxypropylmethylcellulose [e.g., hypromellose 2910, TC-5 (grade: MW, E, EW, R, RW) (trade name); Shin-Etsu Chemical Co., Ltd.], hydroxyethylcellulose, methylhydroxyethylcellulose and the like; synthetic polymers such as polyvinylacetal diethylaminoacetate, aminoalkyl methacrylate copolymer E [Eudragit E (trade name)], polyvinylpyrrolidone and the like; polysaccharides such as pullulan and the like; and so on.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; natural products such as shellac and the like; and so on.

Examples of the sustained-release film coating base include cellulose polymers such as ethylcellulose and the like; acrylic acid polymers such as aminoalkyl methacrylate copolymer RS [Eudragit RS (trade name)], ethyl acrylate-methyl methacrylate copolymer suspension [Eudragit NE (trade name)] and the like; and so on.

Preferable examples of the coating additives include light protecting agents such as titanium oxide and the like; glidants such as talc and the like; colorants such as red ferric oxide, yellow ferric oxide and the like; plasticizers such as macrogol 6000, triethyl citrate, castor oil, polysorbates and the like; organic acids such as citric acid, tartaric acid, malic acid, ascorbic acid and the like; and so on.

The above-mentioned additive may be a mixture of two or more kinds at an appropriate ratio.

The solid preparation of the present invention and the solid preparation P of the present invention preferably further contain crystalline cellulose to optimize physicochemical property (e.g., manufacturability, tablet disintegration property, tablet hardness) of the preparations.

When the solid preparation of the present invention and the solid preparation P of the present invention contain crystalline cellulose, the content of crystalline cellulose in the solid preparations is generally 1-30 wt %, preferably 2-15 wt %, more preferably 3-10 wt %.

The solid preparation of the present invention and the solid preparation P of the present invention preferably further contain croscarmellose sodium to optimize physicochemical property (e.g., manufacturability, tablet disintegration property, tablet hardness) of the preparations.

When the solid preparation of the present invention and the solid preparation P of the present invention contain croscarmellose sodium, the content of croscarmellose sodium in the solid preparations is generally 1-30 wt %, preferably 2-20 wt %, more preferably 5-15 wt %.

The solid preparation of the present invention and the solid preparation P of the present invention preferably further contain hydroxypropylcellulose to optimize physicochemical property (e.g., manufacturability, tablet disintegration property, tablet hardness) of the preparations.

When the solid preparation of the present invention and the solid preparation P of the present invention contain hydroxypropylcellulose, the content of hydroxypropylcellulose in the solid preparations is generally 0.5-15 wt %, preferably 1-10 wt %, more preferably 2-5 wt %.

The solid preparation of the present invention is preferably the following preparation.

[Solid Preparation 1]
A solid preparation comprising
(1) compound (A) or a salt thereof,
(2) sugar alcohol (preferably, mannitol),
(3) sodium stearyl fumarate,
(4) excipient (preferably, crystalline cellulose),
(5) disintegrant (preferably, croscarmellose sodium) and
(6) binder (preferably, hydroxypropylcellulose).

[Solid Preparation 2]
A solid preparation comprising
(1) compound (A) or a salt thereof,
(2) mannitol,
(3) sodium stearyl fumarate,
(4) crystalline cellulose,
(5) croscarmellose sodium and
(6) hydroxypropylcellulose.
[Solid Preparation 3]
A solid preparation comprising
(1) compound (A) or a salt thereof,
(2) sugar alcohol (preferably, mannitol),
(3) sodium stearyl fumarate,
(4) excipient (preferably, crystalline cellulose),
(5) disintegrant (preferably, croscarmellose sodium) and
(6) binder (preferably, hydroxypropylcellulose), wherein the content of compound (A) or a salt thereof is 50-60 wt % (preferably 52-56 wt %) as compound (A) (free form).

Furthermore, the present invention provides the solid preparation P, that is, a solid preparation comprising
(1) 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof,
(2) a saccharide and
(3) stearic acid or talc
in a naked tablet part.

When the solid preparation P of the present invention comprises stearic acid, the content of stearic acid in the solid preparation P is generally 0.3-7 wt %, preferably 0.5-5 wt %, more preferably 1.0-3.0 wt %.

When the solid preparation P of the present invention comprises talc, the content of talc in the solid preparation P is generally 0.3-7 wt %, preferably 0.5-5 wt %, more preferably 1.0-3.0 wt %.

The solid preparation P of the present invention is preferably the following preparation.
[Solid Preparation P-1A]
A solid preparation comprising
(1) compound (A) or a salt thereof,
(2) sugar alcohol (preferably, mannitol),
(3) stearic acid,
(4) excipient (preferably, crystalline cellulose),
(5) disintegrant (preferably, croscarmellose sodium) and
(6) binder (preferably, hydroxypropylcellulose)
in a naked tablet part.
[Solid Preparation P-2A]
A solid preparation comprising
(1) compound (A) or a salt thereof,
(2) mannitol,
(3) stearic acid,
(4) crystalline cellulose,
(5) croscarmellose sodium and
(6) hydroxypropylcellulose
in a naked tablet part.
[Solid Preparation P-1B]
A solid preparation comprising
(1) compound (A) or a salt thereof,
(2) sugar alcohol (preferably, mannitol),
(3) talc,
(4) excipient (preferably, crystalline cellulose),
(5) disintegrant (preferably, croscarmellose sodium) and
(6) binder (preferably, hydroxypropylcellulose)
in a naked tablet part.
[Solid Preparation P-2B]
A solid preparation comprising
(1) compound (A) or a salt thereof,
(2) mannitol,
(3) talc,
(4) crystalline cellulose,
(5) croscarmellose sodium and
(6) hydroxypropylcellulose in a naked tablet part.

Examples of the dosage form of the solid preparation of the present invention and the solid preparation P of the present invention include granule, tablet (e.g., naked tablet, film-coated tablet) and the like. Of these, tablet is preferable.

The solid preparation of the present invention and the solid preparation P of the present invention can be produced by a method conventionally used in the pharmaceutical field.

The solid preparation of the present invention and the solid preparation P of the present invention are specifically produced by appropriately combining operations such as granulation, mixing, tableting (compression molding), coating and the like.

Granulation is performed using, for example, a granulation machine such as a high-shear granulator, a fluid bed granulator, a dry granulating machine or the like.

Mixing is performed using, for example, a mixer such as a V-type mixer, a tumbler mixer or the like.

Tableting (compression molding) is performed by punching using, for example, a single punch tableting machine, a rotary tableting machine and the like, at a pressure of generally 0.3-35 kN/cm$^2$.

Coating is performed using, for example, a film coating apparatus together with the aforementioned coating base and coating additive.

The solid preparation of the present invention and the solid preparation P of the present invention are preferably film coated for the purpose of improving easy administrability, hardness and the like.

Preferable examples of the coating base and coating additive to be used for the film coating include those similar to the ones used for the aforementioned additive.

When the solid preparation of the present invention and the solid preparation P of the present invention are film-coated, the film coating layer is formed in a proportion of generally 1-10 parts by weight, preferably 2-6 parts by weight, per 100 parts by weight of the solid preparation.

Specifically, the solid preparation of the present invention can be produced according to the following production steps. Each starting material in the following production steps is used in such amount as to achieve the aforementioned content in the finally obtained solid preparation.

Compound (A) or a salt thereof and a saccharide are mixed together with other additives (e.g., excipient, binder, disintegrant) as necessary in an appropriate blending machine, and the mixture is granulated using an aqueous solution of a binder (e.g., hydroxypropylcellulose and the like), and sieved when desired. To the obtained sieved powder are added sodium stearyl fumarate and a disintegrant (e.g., croscarmellose sodium and the like), the mixture is molded and dried when desired to give the solid preparation of the present invention. Furthermore, a film coating solution is sprayed when desired to give a film-coated tablet. Mixing and granulation can be performed using, for example, a fluid bed dryer granulator and the like. Molding can be performed by tableting using, for example, a rotary tableting machine.

The solid preparation P of the present invention can be produced in a similar manner to the production method of the solid preparation of the present invention, except that sodium stearyl fumarate is replaced by stearic acid or talc.

A film-coated tablet can be produced by, for example, coating a naked tablet obtained by the above-mentioned method by spraying an aqueous solution of a film coating agent (e.g., a mixture of film coating base such as hypromellose 2910 and the like, plasticizer such as macrogol 6000 and the like, and dye such as titanium oxide, red ferric oxide, yellow ferric oxide and the like) by a film coating machine and the like.

The solid preparation of the present invention and the solid preparation P of the present invention are preferably produced by a fluid bed granulation method. A solid preparation produced by a fluid bed granulation method, particularly a tablet, shows a remarkable effect of the present invention.

The solid preparation of the present invention and the solid preparation P of the present invention are preferably tablets containing granules (e.g., granules obtained by the above-mentioned granulation) at preferably 75-100 wt %, more preferably 80-98 wt %, further preferably 85-95 wt %.

The "granule" here means particles having almost the same size and shape, which are obtained by granulating a starting material in the form of powder, bulk, solution, molten liquid and the like by a wet granulation method, a dry granulation method, a heating granulation method (preferably, dry granulation method) and the like.

The granules generally have a particle size of not less than 1000 μm for not more than 20%, not more than 150 μm for not more than 65% (on (remaining on sieves) with 16 M sieves: not more than 20%; pass (pass through sieves) with 100 M sieves: not more than 65%), preferably not less than 1000 μm for not more than 5%, not more than 150 μm for not more than 55% (on with 16 M sieves: not more than 5%; pass with 100 M sieves: not more than 55%). Here, the particle size is, for example, a value obtained by measuring the weight of the granules remaining on the standard sieves after passage therethrough.

The granules may have different sizes and shapes during the process of preparation making (e.g., tableting step) to give the solid preparation of the present invention and the solid preparation P of the present invention.

The weight of the solid preparation of the present invention and the solid preparation P of the present invention per unit dosage form (for example, per tablet) is generally 50-500 mg, preferably 70-350 mg, more preferably 80-200 mg.

The solid preparation of the present invention and the solid preparation P of the present invention have excellent effect as medicaments, and particularly show excellent inhibitory activity on dipeptidyl peptidase (DPP-IV). Since the solid preparation of the present invention and the solid preparation P of the present invention are low in toxicity and have fewer side effects, they are useful for mammals (e.g., human, bovine, horse, swine, dog, cat, monkey, mouse, rat, particularly human) in the prophylaxis or treatment of, for example, diabetes [e.g., type 1 diabetes, type 2 diabetes, type 1.5 diabetes (LADA (Latent Autoimmune Diabetes in Adults)), gestational diabetes, diabetes with impaired insulin secretion, obese diabetes, IGT (impaired glucose tolerance), IFG (Impaired Fasting Glucose), IFG (Impaired Fasting Glycaemia)], diabetic complications [e.g., neuropathy, nephropathy, retinopathy, cataract, macroangiopathy, arteriosclerosis, osteopenia, hyperosmolar diabetic coma, infections (e.g., respiratory infection, urinary tract infection, gastrointestinal infection, dermal soft tissue infection, inferior limb infection), diabetic gangrene, xerostomia, hypacusis, cerebrovascular disorder, peripheral blood circulation disorder], obesity, hyperlipidemia (e.g., hypertriglyceridemia, hypercholesterolemia, hypoHDL-emia, postprandial hyperlipemia), arteriosclerosis (e.g., atherosclerosis), hypertension, myocardial infarction, angina pectoris, cerebrovascular disorder (e.g., cerebral infarction, cerebral apoplexy), insulin resistance syndrome, syndrome X, dysmetabolic syndrome and the like.

In addition, the solid preparation of the present invention and the solid preparation P of the present invention are also useful for secondary prevention of the above-mentioned various diseases (e.g., secondary prevention of cardiovascular event such as myocardial infarction and the like) or suppression of progression [e.g., suppression of progression from impaired glucose tolerance to diabetes; suppression of progression from diabetes to diabetic complications (preferably diabetic neuropathy, diabetic nephropathy, diabetic retinopathy, arteriosclerosis)].

The solid preparation of the present invention and the solid preparation P of the present invention can be administered orally and safely to a mammal.

The dose of the solid preparation of the present invention and the solid preparation P of the present invention only need to contain an effective amount of compound (A) or a salt thereof as a pharmaceutically active ingredient. For example, for administration to an adult (body weight 60 kg) at intervals of more than one day (e.g., once in 3 days-1 week), the effective amount is generally 1 mg-500 mg, preferably 1 mg-400 mg, more preferably 25 mg-250 mg, further preferably 50 mg-200 mg, per unit administration as compound (A) free form. For example, when one dose of compound (A) or a salt thereof is 50 mg as compound (A) free form, the present invention can provide a solid preparation having a total weight of within 100 mg per tablet.

Since the solid preparation of the present invention and the solid preparation P of the present invention contain compound (A) or a salt thereof at a high dose, and have a size for easy administration, they are preferable for administration of compound (A) or a salt thereof at a high dose. For example, the solid preparation of the present invention and the solid preparation P of the present invention are preferable for administration at intervals of more than one day (preferably, once a week), and can be provided as a dosage form of once in 3 days to 2 weeks (preferably, dosage form of once per week).

While the size of the solid preparation of the present invention and the solid preparation P of the present invention varies depending on the shape of the solid preparation (round, caplet, oblong etc.), it may be any size as long as patients can take with ease. For example, when the shape of the solid preparation is oblong, the size of the major axis of the solid preparation is preferably not less than 6 mm and not more than 13 mm, more preferably not less than 7 mm and not more than 12 mm. When the shape of the solid preparation is round, the diameter of the solid preparation is preferably not less than 4 mm and not more than 9 mm, more preferably not less than 5 mm and not more than 8 mm.

Particularly preferable specific examples of the solid preparation of the present invention and the solid preparation P of the present invention include "a solid preparation containing compound (A) or a salt thereof at 50 mg per tablet as compound (A) (free form)";

"a solid preparation containing compound (A) or a salt thereof at 100 mg per tablet as compound (A) (free form)"; and "a solid preparation containing compound (A) or a salt thereof at 200 mg per tablet as compound (A) (free form)".

The solid preparation of the present invention and the solid preparation P of the present invention can be used in combination with one or more different kinds of medicaments (hereinafter sometimes to be abbreviated as "concomitant drug").

Specific examples of the concomitant drug include one or more medicaments selected from a therapeutic agent for diabetes, a therapeutic agent for diabetic complications, a therapeutic agent for hyperlipidemia, an antihypertensive agent, an antiobesity agent, a diuretic, an antithrombotic agent and the like.

Examples of the therapeutic agent for diabetes include insulin preparations (e.g., animal insulin preparation extracted from the pancreas of bovine, swine; human insulin preparation synthesized by genetic engineering using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), metaglidasen, AMG-131, balaglitazone, MBX-2044, rivoglitazone, aleglitazar, chiglitazar, lobeglitazone, PLX-204, PN-2034, GFT-505, THR-0921, compounds described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., alogliptin or a salt thereof (preferably benzoate), vildagliptin, sitagliptin, saxagliptin, BI1356, GRC8200, MP-513, PF-00734200, PHX1149, SK-0403, ALS2-0426, TA-6666, TS-021, KRP-104), β3 agonists (e.g., N-5984), GPR40 agonists (e.g., fasiglifam or hydrate thereof, compounds described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1MR agent, liraglutide, exenatide, AVE-0010, BIM-51077, Aib(8,35)hGLP-1(7,37)NH2, CJC-1131, albiglutide), amylin agonists (e.g., pramlintide), phosphotyrosine phosphatase inhibitors (e.g., sodium vanadate), gluconeogenesis inhibitors (e.g., glycogen phosphorylase inhibitor, glucose-6-phosphatase inhibitor, glucagon antagonist, FBPase inhibitor), SGLT2 (sodium-glucose cotransporter 2) inhibitors (e.g., depagliflozin, AVE2268, TS-033, YM543, TA-7284, remogliflozin, ASP1941), SGLT1 inhibitors, 11β-hydroxysteroid dehydrogenase inhibitors (e.g., BVT-3498, INCB-13739), adiponectin or agonist thereof, IKK inhibitors (e.g., AS-2868), leptin resistance improving drugs, somatostatin receptor agonists, glucokinase activators (e.g., piragliatin, AZD1656, AZD6370, TTP-355, compounds described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF21, FGF analogue and the like.

Examples of the therapeutic agents for diabetic complications include aldose reductase inhibitors (e.g., tolrestat, epalrestat, zopolrestat, fidarestat, CT-112, ranirestat (AS-3201), lidorestat), neurotrophic factors and increasing drugs thereof (e.g., NGF, NT-3, BDNF, neurotrophin production/secretion promoting agent described in WO01/14372 (e.g., 4-(4-chlorophenyl)-2-(2-methyl-1-imidazolyl)-5-[3-(2-methylphenoxy)propyl]oxazole), compounds described in WO2004/039365), PKC inhibitors (e.g., ruboxistaurin mesylate), AGE inhibitors (e.g., ALT946, N-phenacylthiazolium bromide (ALT766), EXO-226, pyridorin, pyridoxamine), GABA receptor agonists (e.g., gabapentin, pregabalin), serotonin noradrenaline reuptake inhibitors (e.g., duloxetine), sodium channel inhibitors (e.g., lacosamide), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitors and the like.

Examples of the therapeutic agent for hyperlipidemia include HMG-CoA reductase inhibitors (e.g., pravastatin, simvastatin, lovastatin, atorvastatin, fluvastatin, rosuvastatin, pitavastatin or salts thereof (e.g., sodium salt, calcium salt)), squalene synthase inhibitors (e.g., compounds described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril, etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil and the like), calcium antagonists (e.g., manidipine, nifedipine, amlodipine, efonidipine, nicardipine, cilnidipine and the like), β blockers (e.g., metoprolol, atenolol, propranolol, carvedilol, pindolol and the like), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor antagonists, GABA modulators (e.g., topiramate), neuropeptide Y (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl-CoA carboxylase (ACC) inhibitors, stearoyl-CoA desaturase inhibitors, microsomal triglyceride transfer protein inhibitors (e.g., R-256918), sodium-glucose cotransporter inhibitors (e.g., JNJ-28431754, remogliflozin), NFκB inhibitors (e.g., HE-3286), PPAR agonists (e.g., GFT-505, DRF-11605), phosphotyrosine phosphatase inhibitors (e.g., sodium vanadate, trodusquemine), GPR119 agonists (e.g., PSN-821), glucokinase activators (e.g., AZD-1656), leptin, leptin derivative (e.g., metreleptin), CNTF (ciliary neurotrophic factor), BDNF (brain-derived neurotrophic factor), cholecystokinin agonists, glucagon-like peptide-1 (GLP-1) preparation (e.g., animal GLP-1 preparation extracted from bovine or swine pancreas; human GLP-1 preparation synthesized by genetic engineering using *Escherichia coli* or yeast; fragment or derivative of GLP-1 (e.g., exenatide, liraglutide), amylin preparation (e.g., pramlintide, AC-2307), neuropeptide Y agonists (e.g., PYY3-36, derivatives of PYY3-36, obinepitide, TM-30339, TM-30335), oxyntomodulin preparation: FGF21 preparations (e.g., animal FGF21 preparation extracted from bovine or swine pancreas; human FGF21 preparation synthesized by genetic engineering using *Escherichia coli* or yeast; fragment or derivative of FGF21), anorexigenic agents (e.g., P-57) and the like.

Examples of the diuretic include xanthine derivatives (e.g., theobromine sodium salicylate, theobromine calcium salicylate, etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonic anhydrase inhibitors (e.g., acetazolamide, etc.), chlorobenzenesulfonamide agents (e.g., chlortalidone, mefruside, indapamide, etc.), azosemide, isosorbide, ethacrynic acid, piretanide, bumetanide, furosemide and the like.

Examples of the antithrombotic agent include heparins (e.g., heparin sodium, heparin calcium, enoxaparin sodium, dalteparin sodium), warfarins (e.g., warfarin potassium), anti-thrombin drugs (e.g., argatroban, dabigatran), FXa inhibitors (e.g., rivaroxaban), apixaban, edoxaban, YM150, compounds described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Of the above-mentioned concomitant drugs, insulin sensitizers (preferably pioglitazone hydrochloride), insulin preparation, α-glucosidase inhibitors (preferably voglibose, acarbose), biguanides (preferably metformin hydrochloride), sulfonylureas (preferably glimepiride) and the like are preferable.

When the solid preparation of the present invention or the solid preparation P of the present invention and a concomitant drug are used in combination, the administration time of these is not limited, and they may be administered simultaneously to a subject of administration, or may be administered with a time difference.

In addition, the solid preparation of the present invention or the solid preparation P of the present invention and the concomitant drug may be administered as separate preparations to an administration subject, or they may be administered to an administration subject as a single preparation containing the solid preparation of the present invention or the solid preparation P of the present invention and the concomitant drug.

The dose of the concomitant drug can be appropriately determined based on the clinically employed dose of each drug. In addition, the mixing ratio of the solid preparation of the present invention or the solid preparation P of the present invention and the concomitant drug can be appropriately determined according to the administration subject, administration route, target disease, condition, combination and the like. For example, when the administration subject is a human, the concomitant drug may be used in an amount of 0.01 to 100 parts by weight per 1 part by weight of the solid preparation of the present invention or the solid preparation P of the present invention.

Use of the concomitant drug in this way provides superior effects such as 1) enhanced effect of the action of compound (A) (or a salt thereof) or a concomitant drug (synergistic effect of medicament actions), 2) reduction effect of the dose of compound (A) (or a salt thereof) or a concomitant drug (reduction effect of medicament dose as compared to single drug administration), 3) reduction effect of secondary action of compound (A) (or a salt thereof) or a concomitant drug, and the like.

EXAMPLES

The present invention is explained in more detail in the following by referring to Examples, Comparative Examples and Experimental Examples, which are not to be construed as limitative.

As additives for pharmaceutical preparations in the following Examples, Comparative Examples and Experimental Examples, the Japanese Pharmacopoeia 16th edition, the Japanese Pharmaceutical Codex or Japanese Pharmaceutical Excipients 2003 compatible products were used.

Example 1

Film-coated tablets (13800 tablets) having the formulation shown in Table 1 were obtained by the following method. In a fluid bed dryer granulator (FD-5S, Powrex Corporation), succinate of compound (A), mannitol, crystalline cellulose and croscarmellose sodium (Ac-Di-Sol, Dainippon Sumitomo Pharma Co., Ltd.) were uniformly mixed, and the mixture was granulated by spraying an aqueous solution of hydroxypropylcellulose (HPC grade L, Nippon Soda Co., Ltd.) and dried therein. The granules were sieved by a granulator (Power Mill P-3, SHOWA KAGAKU KIKAI CO., LTD.) to give a sieved powder. To the sieved powder were added croscarmellose sodium (Ac-Di-Sol, Dainippon Sumitomo Pharma Co., Ltd.) and sodium stearyl fumarate and they were mixed in a blending machine (Tumbler 15L, SHOWA KAGAKU KIKAI CO., LTD.) to give granules for tableting. The granules were tableted by a rotary tableting machine (Correct 12HUK, Kikusui Seisakusho Ltd.) using a 10.8×5.4 mm punch to give a naked tablet (180 mg). In an aqueous solution of hypromellose 2910 and macrogol 6000 were dispersed titanium oxide and red ferric oxide to give a film coating solution. The aforementioned coating solution was sprayed on the abovementioned naked tablet in a film coating machine (DRIA-COATER DRC500, Powrex Corporation) to give film-coated tablets containing 100 mg of succinate of compound (A) per tablet as compound (A) (free form).

TABLE 1

| component (mg/tablet) | compound (A) free form 100 mg |
|---|---|
| naked tablet | |
| succinate of compound (A) | 133 |
| mannitol | 11 |
| crystalline cellulose | 9 |
| croscarmellose sodium | 18 |
| hydroxypropylcellulose | 5.4 |
| sodium stearyl fumarate | 3.6 |
| film coating | |
| hypromellose 2910 | 4.95 |
| macrogol 6000 | 1.1 |
| titanium oxide | 0.55 |
| red ferric oxide | 0.01 |
| total | 186.61 |

Example 2

Naked tablets (30 tablets) having the formulation shown in Table 2 were obtained by the following method. In a fluid bed dryer granulator (FD-WSG-30, Powrex Corporation) and according to the formulation of Table 2, succinate of compound (A), mannitol, crystalline cellulose and croscarmellose sodium (Ac-Di-Sol, Dainippon Sumitomo Pharma Co., Ltd.) were uniformly mixed, and the mixture was granulated by spraying an aqueous solution of hydroxypropylcellulose (HPC grade L, Nippon Soda Co., Ltd.) and dried therein. The granules were sieved by a granulator (Power Mill P-3, SHOWA KAGAKU KIKAI CO., LTD.) to give a sieved powder. To the sieved powder were added croscarmellose sodium (Ac-Di-Sol, Dainippon Sumitomo Pharma Co., Ltd.) and sodium stearyl fumarate and they were mixed in a bottle to give granules for tableting. The granules were tableted by a desktop tablet press machine (HANDTAB200, Ichihashi Seiki Co., Ltd.) using a 10.8×5.4 mm punch to give a naked tablet (mass 180 mg) containing 100 mg of succinate of compound (A) per tablet as compound (A) (free form).

TABLE 2

| component (mg/tablet) | compound (A) free form 100 mg |
|---|---|
| naked tablet | |
| succinate of compound (A) | 133 |
| mannitol | 11 |
| crystalline cellulose | 9 |
| croscarmellose sodium | 18 |
| hydroxypropylcellulose | 5.4 |
| sodium stearyl fumarate | 3.6 |
| total | 180 |

Example 3

Naked tablets (30 tablets) having the formulation shown in Table 3 were obtained by the following method. In a fluid bed dryer granulator (FD-WSG-30, Powrex Corporation) and according to the formulation of Table 3, succinate of compound (A), mannitol, crystalline cellulose and croscarmellose sodium (Ac-Di-Sol, Dainippon Sumitomo Pharma Co., Ltd.) were uniformly mixed, and the mixture was granulated by spraying an aqueous solution of hydroxypropylcellulose (HPC grade L, Nippon Soda Co., Ltd.) and dried therein. The granules were sieved by a granulator (Power Mill P-3, SHOWA KAGAKU KIKAI CO., LTD.) to give a sieved powder. To the sieved powder were added croscarmellose sodium (Ac-Di-Sol, Dainippon Sumitomo Pharma Co., Ltd.) and stearic acid and they were mixed in a bottle to give granules for tableting. The granules were tableted by a desktop tablet press machine (HANDTAB200, Ichihashi Seiki Co., Ltd.) using a 10.8×5.4 mm punch to give a naked tablet (mass 180 mg) containing 100 mg of succinate of compound (A) per tablet as compound (A) (free form).

TABLE 3

| component (mg/tablet) | compound (A) free form 100 mg |
|---|---|
| naked tablet | |
| succinate of compound (A) | 133 |
| mannitol | 11 |
| crystalline cellulose | 9 |
| croscarmellose sodium | 18 |

TABLE 3-continued

| component (mg/tablet) | compound (A) free form 100 mg |
|---|---|
| hydroxypropylcellulose | 5.4 |
| stearic acid | 3.6 |
| total | 180 |

Example 4

Naked tablets (30 tablets) having the formulation shown in Table 4 were obtained by the following method. In a fluid bed dryer granulator (FD-WSG-30, Powrex Corporation) and according to the formulation of Table 4, succinate of compound (A), mannitol, crystalline cellulose and croscarmellose sodium (Ac-Di-Sol, Dainippon Sumitomo Pharma Co., Ltd.) were uniformly mixed, and the mixture was granulated by spraying an aqueous solution of hydroxypropylcellulose (HPC grade L, Nippon Soda Co., Ltd.) and dried therein. The granules were sieved by a granulator (Power Mill P-3, SHOWA KAGAKU KIKAI CO., LTD.) to give a sieved powder. To the sieved powder were added croscarmellose sodium (Ac-Di-Sol, Dainippon Sumitomo Pharma Co., Ltd.) and talc and they were mixed in a bottle to give granules for tableting. The granules were tableted by a desktop tablet press machine (HANDTAB200, Ichihashi Seiki Co., Ltd.) using a 10.8×5.4 mm punch to give a naked tablet (mass 180 mg) containing 100 mg of succinate of compound (A) per tablet as compound (A) (free form).

TABLE 4

| component (mg/tablet) | compound (A) free form 100 mg |
|---|---|
| naked tablet | |
| succinate of compound (A) | 133 |
| mannitol | 11 |
| crystalline cellulose | 9 |
| croscarmellose sodium | 18 |
| hydroxypropylcellulose | 5.4 |
| talc | 3.6 |
| total | 180 |

Comparative Example 1

Film-coated tablets (555 tablets) having the formulation shown in Table 5 were obtained by the following method. In a fluid bed dryer granulator (LAB-1, Powrex Corporation), succinate of compound (A), mannitol, crystalline cellulose and croscarmellose sodium (Ac-Di-Sol, Dainippon Sumitomo Pharma Co., Ltd.) were uniformly mixed, and the mixture was granulated by spraying an aqueous solution of hydroxypropylcellulose (HPC grade L, Nippon Soda Co., Ltd.) and dried therein. The obtained granules were sieved with sieve (16 M) to give a sieved powder. To the sieved powder were added croscarmellose sodium (Ac-Di-Sol, Dainippon Sumitomo Pharma Co., Ltd.) and magnesium stearate and they were mixed in a bag to give granules for tableting. The granules were tableted by a rotary tableting machine (Correct 19K, Kikusui Seisakusho Ltd.) using a 10.8×5.4 mm punch to give a naked tablet (180 mg). An aqueous dispersion of OPADRY White (Colorcon Japan, LLC; containing hypromellose 2910, macrogol 6000 and titanium oxide) and OPADRY Red (Colorcon Japan, LLC; containing hypromellose 2910, macrogol 6000, titanium oxide and red ferric oxide) was prepared as a film coating solution. The aforementioned coating solution was sprayed on the above-mentioned naked tablet in a film coating machine (DRIACOATER DRC200, Powrex Corporation) to give film-coated tablets containing 100 mg of succinate of compound (A) per tablet as compound (A) (free form).

TABLE 5

| component (mg/tablet) | compound (A) free form 100 mg |
|---|---|
| naked tablet | |
| succinate of compound (A) | 133 |
| mannitol | 11.9 |
| crystalline cellulose | 9 |
| croscarmellose sodium | 18 |
| hydroxypropylcellulose | 5.4 |
| magnesium stearate | 3.6 |
| film coating | |
| OPADRY White | 6.174 |
| OPADRY Red | 0.686 |
| total | 187.76 |

Comparative Example 2

Naked tablets (30 tablets) having the formulation shown in Table 6 were obtained by the following method. In a fluid bed dryer granulator (FD-WSG-30, Powrex Corporation) and according to the formulation of Table 6, succinate of compound (A), mannitol, crystalline cellulose and croscarmellose sodium (Ac-Di-Sol, Dainippon Sumitomo Pharma Co., Ltd.) were uniformly mixed, and the mixture was granulated by spraying an aqueous solution of hydroxypropylcellulose (HPC grade L, Nippon Soda Co., Ltd.) and dried therein. The granules were sieved by a granulator (Power Mill P-3, SHOWA KAGAKU KIKAI CO., LTD.) to give a sieved powder. To the sieved powder were added croscarmellose sodium (Ac-Di-Sol, Dainippon Sumitomo Pharma Co., Ltd.) and magnesium stearate and they were mixed in a bottle to give granules for tableting. The granules were tableted by a desktop tablet press machine (HANDTAB200, Ichihashi Seiki Co., Ltd.) using a 10.8×5.4 mm punch to give a naked tablet (mass 180 mg) containing 100 mg of succinate of compound (A) per tablet as compound (A) (free form).

TABLE 6

| component (mg/tablet) | compound (A) free form 100 mg |
|---|---|
| naked tablet | |
| succinate of compound (A) | 133 |
| mannitol | 11 |
| crystalline cellulose | 9 |
| croscarmellose sodium | 18 |
| hydroxypropylcellulose | 5.4 |
| magnesium stearate | 3.6 |
| total | 180 |

Comparative Example 3

Naked tablets (30 tablets) having the formulation shown in Table 7 were obtained by the following method. In a fluid bed dryer granulator (FD-WSG-30, Powrex Corporation) and according to the formulation of Table 7, succinate of compound (A), mannitol, crystalline cellulose and croscarmellose sodium (Ac-Di-Sol, Dainippon Sumitomo Pharma Co., Ltd.) were uniformly mixed, and the mixture was granulated by spraying an aqueous solution of hydroxypropylcellulose (HPC grade L, Nippon Soda Co., Ltd.) and dried therein. The granules were sieved by a granulator (Power Mill P-3, SHOWA KAGAKU KIKAI CO., LTD.) to give a sieved powder. To the sieved powder were added croscarmellose sodium (Ac-Di-Sol, Dainippon Sumitomo Pharma Co., Ltd.) and calcium stearate and they were mixed in a bottle to give granules for tableting. The granules were tableted by a desktop tablet press machine (HANDTAB200, Ichihashi Seiki Co., Ltd.) using a 10.8×5.4 mm punch to give a naked tablet (mass 180 mg) containing 100 mg of succinate of compound (A) per tablet as compound (A) (free form).

TABLE 7

| component (mg/tablet) | compound (A) free form 100 mg |
|---|---|
| naked tablet | |
| succinate of compound (A) | 133 |
| mannitol | 11 |
| crystalline cellulose | 9 |
| croscarmellose sodium | 18 |
| hydroxypropylcellulose | 5.4 |
| calcium stearate | 3.6 |
| total | 180 |

Comparative Example 4

Naked tablets (30 tablets) having the formulation shown in Table 8 were obtained by the following method. In a fluid bed dryer granulator (FD-WSG-30, Powrex Corporation) and according to the formulation of Table 8, succinate of compound (A), mannitol, crystalline cellulose and croscarmellose sodium (Ac-Di-Sol, Dainippon Sumitomo Pharma Co., Ltd.) were uniformly mixed, and the mixture was granulated by spraying an aqueous solution of hydroxypropylcellulose (HPC grade L, Nippon Soda Co., Ltd.) and dried therein. The granules were sieved by a granulator (Power Mill P-3, SHOWA KAGAKU KIKAI CO., LTD.) to give a sieved powder. To the sieved powder were added croscarmellose sodium (Ac-Di-Sol, Dainippon Sumitomo Pharma Co., Ltd.) and sucrose ester of fatty acid and they were mixed in a bottle to give granules for tableting. The granules were tableted by a desktop tablet press machine (HANDTAB200, Ichihashi Seiki Co., Ltd.) using a 10.8×5.4 mm punch to give a naked tablet (mass 180 mg) containing 100 mg of succinate of compound (A) per tablet as compound (A) (free form).

TABLE 8

| component (mg/tablet) | compound (A) free form 100 mg |
|---|---|
| naked tablet | |
| succinate of compound (A) | 133 |
| mannitol | 11 |
| crystalline cellulose | 9 |
| croscarmellose sodium | 18 |
| hydroxypropylcellulose | 5.4 |
| sucrose ester of fatty acid | 3.6 |
| total | 180 |

Comparative Example 5

Naked tablets (30 tablets) having the formulation shown in Table 9 were obtained by the following method. In a fluid bed dryer granulator (FD-WSG-30, Powrex Corporation) and according to the formulation of Table 9, succinate of compound (A), mannitol, crystalline cellulose and croscarmellose sodium (Ac-Di-Sol, Dainippon Sumitomo Pharma Co., Ltd.) were uniformly mixed, and the mixture was granulated by spraying an aqueous solution of hydroxypropylcellulose (HPC grade L, Nippon Soda Co., Ltd.) and dried therein. The granules were sieved by a granulator (Power Mill P-3, SHOWA KAGAKU KIKAI CO., LTD.) to give a sieved powder. To the sieved powder were added croscarmellose sodium (Ac-Di-Sol, Dainippon Sumitomo Pharma Co., Ltd.) and glycerol fatty acid ester (COMPRITOL 888ATO) and they were mixed in a bottle to give granules for tableting. The granules were tableted by a desktop tablet press machine (HANDTAB200, Ichihashi Seiki Co., Ltd.) using a 10.8×5.4 mm punch to give a naked tablet (mass 180 mg) containing 100 mg of succinate of compound (A) per tablet as compound (A) (free form).

TABLE 9

| component (mg/tablet) | compound (A) free form 100 mg |
|---|---|
| naked tablet | |
| succinate of compound (A) | 133 |
| mannitol | 11 |
| crystalline cellulose | 9 |
| croscarmellose sodium | 18 |
| hydroxypropylcellulose | 5.4 |
| glycerol fatty acid ester | 3.6 |
| total | 180 |

Experimental Example 1

The film-coated tablets of Example 1 and Comparative Example 1 were humidity-conditioned at 75% RH, placed in a glass bottle, preserved at 60° C. for 2 weeks, and the dissolution property of compound (A) was measured according to the Japanese Pharmacopoeia Paddle Method (50 rpm, 37° C., 2nd fluid for dissolution test of the Japanese Pharmacopoeia 900 mL, n=3). The results are shown in Table 10. The values in the Table each show an average dissolution ratio of 3 film-coated tablets.

TABLE 10

| | | Example 1 | | Comparative Example 1 | |
|---|---|---|---|---|---|
| | | preservation experiment initial | 2 week preservation | preservation experiment initial | 2 week preservation |
| dissolution ratio (%) | 0 min | 0 | 0 | 0 | 0 |
| | 10 min | 89 | 88 | 80 | 18 |
| | 15 min | 99 | 99 | 94 | 32 |
| | 20 min | 102 | 101 | 97 | 45 |
| | 30 min | 103 | 101 | 99 | 70 |
| | 45 min | 103 | 101 | 99 | 92 |

As shown in Table 10, the film-coated tablet of Comparative Example 1 showed delayed dissolution of compound (A) between before and after the preservation. In contrast, the film-coated tablet of Example 1 showed almost no changes in the dissolution property of compound (A) before and after the preservation and was stable.

Experimental Example 2

The film-coated tablets of Example 1 and Comparative Example 1 were humidity-conditioned at 75% RH, placed in a glass bottle, preserved at 60° C. for 2 weeks, and the disintegration property of the film-coated tablet was measured according to the Japanese Pharmacopoeia Disintegration Test Method (37° C., water, n=6). The results are shown in Table 11. The values in the Table each show an average disintegration time of 6 film-coated tablets.

TABLE 11

| | Example 1 | | Comparative Example 1 | |
|---|---|---|---|---|
| | preservation experiment initial | 2 week preservation | preservation experiment initial | 2 week preservation |
| disintegration time (min) | 4.5 | 5.4 | 6.1 | 41.0 |

As shown in Table 11, the film-coated tablet of Comparative Example 1 showed delayed disintegration between before and after the preservation. In contrast, the film-coated tablet of Example 1 showed almost no changes in the disintegration property before and after the preservation and was stable.

Experimental Example 3

The tablets of Examples 2 to 4 and Comparative Examples 2 to 5 were humidity-conditioned at 75% RH, placed in a glass bottle, preserved at 60° C. for 2 weeks, and the dissolution property of compound (A) was measured according to the Japanese Pharmacopoeia Paddle Method (50 rpm, 37° C., 2nd fluid for dissolution test of the Japanese Pharmacopoeia 900 mL, n=3). The results are shown in Tables 12 and 13. The values in the Table each show an average dissolution ratio of 3 tablets.

TABLE 12

|  |  | Example 2 | | Example 3 | | Example 4 | |
| --- | --- | --- | --- | --- | --- | --- | --- |
|  |  | preservation experiment initial | 2 week preservation | preservation experiment initial | 2 week preservation | preservation experiment initial | 2 week preservation |
| dissolution ratio (%) | 0 min | 0 | 0 | 0 | 0 | 0 | 0 |
|  | 10 min | 81 | 71 | 80 | 70 | 86 | 84 |
|  | 15 min | 96 | 88 | 94 | 88 | 96 | 96 |
|  | 20 min | 100 | 95 | 99 | 96 | 99 | 99 |

TABLE 13

|  |  | Comparative Example 2 | | Comparative Example 3 | | Comparative Example 4 | | Comparative Example 5 | |
| --- | --- | --- | --- | --- | --- | --- | --- | --- | --- |
|  |  | preservation experiment initial | 2 week preservation | preservation experiment initial | 2 week preservation | preservation experiment initial | 2 week preservation | preservation experiment initial | 2 week preservation |
| dissolution ratio (%) | 0 min | 0 | 0 | 0 | 0 | 0 | 0 | 0 | 0 |
|  | 10 min | 69 | 47 | 82 | 50 | 83 | 36 | 87 | 57 |
|  | 15 min | 88 | 67 | 96 | 72 | 95 | 52 | 100 | 76 |
|  | 20 min | 96 | 86 | 99 | 85 | 99 | 63 | 101 | 89 |

As shown in Tables 12 and 13, the tablets of Comparative Examples 2 to 5 showed delayed dissolution of compound (A) between before and after the preservation. In contrast, the tablets of Examples 2 to 4 showed almost no changes in the dissolution property of compound (A) before and after the preservation and were stable.

Experimental Example 4

The tablets of Examples 2 to 4 and Comparative Examples 2 to 5 were humidity-conditioned at 75% RH, placed in a glass bottle, preserved at 60° C. for 2 weeks, and the disintegration property of the tablet was measured according to the Japanese Pharmacopoeia Disintegration Test Method (37° C., water, n=6). The results are shown in Tables 14 and 15. The values in the Table each show an average disintegration time of 6 tablets.

TABLE 14

|  | Example 2 | | Example 3 | | Example 4 | |
| --- | --- | --- | --- | --- | --- | --- |
|  | preservation experiment initial | 2 week preservation | preservation experiment initial | 2 week preservation | preservation experiment initial | 2 week preservation |
| disintegration time (min) | 3.3 | 3.8 | 4.7 | 5.0 | 2.8 | 2.9 |

TABLE 15

|  | Comparative Example 2 | | Comparative Example 3 | | Comparative Example 4 | | Comparative Example 5 | |
| --- | --- | --- | --- | --- | --- | --- | --- | --- |
|  | preservation experiment initial | 2 week preservation | preservation experiment initial | 2 week preservation | preservation experiment initial | 2 week preservation | preservation experiment initial | 2 week preservation |
| disintegration time (min) | 6.4 | 7.9 | 4.6 | 8.8 | 3.7 | 18.8 | 3.7 | 5.4 |

As shown in Tables 14 and 15, the tablets of Comparative Examples 2 to 5 showed delayed disintegration between before and after the preservation. In contrast, the tablets of Examples 2 to 4 showed almost no changes in the disintegration property before and after the preservation and were stable.

INDUSTRIAL APPLICABILITY

According to the present invention, a solid preparation comprising 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof as an active ingredient in a high content (not less than 50 wt %), which is excellent in the disintegration property and preservation stability, can be provided.

This application is based on a patent application No. 2012-128360 filed in Japan, the contents of which are incorporated by reference in full herein.

The invention claimed is:
1. A solid preparation comprising
   (1) 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof,
   (2) a saccharide and
   (3) sodium stearyl fumarate.
2. The solid preparation according to claim 1, wherein the saccharide is mannitol.
3. The solid preparation according to claim 1, wherein the content of 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof is 50-60 wt % as 2-[[6-[(3R)-3-amino-1-piperidinyl]-3,4-dihydro-3-methyl-2,4-dioxo-1(2H)-pyrimidinyl]methyl]-4-fluorobenzonitrile in free form.
4. The solid preparation according to claim 1, further comprising crystalline cellulose, croscarmellose sodium and hydroxypropylcellulose.
5. The solid preparation according to claim 3, wherein the saccharide is mannitol.
6. The solid preparation according to claim 3, further comprising crystalline cellulose, croscarmellose sodium and hydroxypropylcellulose.
7. The solid preparation according to claim 1, wherein the 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof is succinate of 2-[[6-[(3R)-3-amino-1-piperidinyl]-3,4-dihydro-3-methyl-2,4-dioxo-1(2H)-pyrimidinyl]methyl]-4-fluorobenzonitrile.
8. The solid preparation according to claim 3, wherein the 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof is succinate of 2-[[6-[(3R)-3-amino-1-piperidinyl]-3,4-dihydro-3-methyl-2,4-dioxo-1(2H)-pyrimidinyl]methyl]-4-fluorobenzonitrile.
9. The solid preparation according to claim 3, wherein the content of 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof is 52-56 wt % as 2-[[6-[(3R)-3-amino-1-piperidinyl]-3,4-dihydro-3-methyl-2,4-dioxo-1(2H)-pyrimidinyl]methyl]-4-fluorobenzonitrile in free form.

* * * * *